(12) United States Patent
Yang et al.

(10) Patent No.: US 9,229,012 B2
(45) Date of Patent: Jan. 5, 2016

(54) SPECIFIC A1AT MONOCLONAL ANTIBODIES FOR DETECTION OF ENDOMETRIOSIS

(71) Applicants: Taipei Medical University, Taipei (TW); Academia Sinica, Taipei (TW)

(72) Inventors: Wei-Chung Yang, Taipei (TW); Hwei-Jiung Wang, Taipei (TW); Shui-Tsung Chen, New Taipei (TW); Ken-Fen Lu, New Taipei (TW); Ming-Chi Peng, Hsinchu County (TW)

(73) Assignees: Taipei Medical University, Taipei (TW); Academia Sinica, Taipei (TW)

( * ) Notice: Subject to any disclaimer, the term of this patent is extended or adjusted under 35 U.S.C. 154(b) by 0 days.

(21) Appl. No.: 13/942,529

(22) Filed: Jul. 15, 2013

(65) Prior Publication Data

US 2013/0288279 A1 Oct. 31, 2013

Related U.S. Application Data

(63) Continuation of application No. PCT/US2012/021315, filed on Jan. 13, 2012.

(60) Provisional application No. 61/433,183, filed on Jan. 14, 2011.

(51) Int. Cl.
| | | |
|---|---|---|
| *G01N 33/53* | (2006.01) | |
| *G01N 33/68* | (2006.01) | |
| *C07K 16/18* | (2006.01) | |
| *C07K 16/38* | (2006.01) | |

(52) U.S. Cl.
CPC ............ *G01N 33/6893* (2013.01); *C07K 16/18* (2013.01); *C07K 16/38* (2013.01); *C07K 2317/34* (2013.01); *G01N 2333/8125* (2013.01); *G01N 2800/364* (2013.01)

(58) Field of Classification Search
None
See application file for complete search history.

(56) References Cited

U.S. PATENT DOCUMENTS 4,444,879 A * 4/1984 Foster et al. ................ 435/7.95
7,807,781 B2 * 10/2010 Shapiro ......................... 530/330

FOREIGN PATENT DOCUMENTS

| TW | 200720657 | 6/2007 |
| TW | I305837 | 2/2009 |

OTHER PUBLICATIONS

Taharaguchi et al., Detection of an isoform of a1-antitrypsin in serum samples from foals with gastric ulcers, The Veterinary Record, Sep. 8, 2007, pp. 338-342.*
Miranda E. et al., "A Novel Monoclonal Antibody to Characterize Pathogenic Polymers in Liver Disease Associated with $\alpha_1$-Antitrypsin Deficiency" Hepatology, 14, Sep. 2010, vol. 52, No. 3, pp. 1078-1088.
Silvestrini B. et al., "Development of an Enzyme-Linked Immunosorbent Assay with a Monoclonal Antibody Prepared against $\alpha_1$-Antitrypsin for Diagnostic Screening of Inflammatory Disorders" Clinical Chemistry, Jan. 1, 1990, vol. 36 No. 2, pp. 277-282.
Janciauskiene S. et al., "Detection of Circulating and Endothelial Cell Polymers of Z and Wild Type $\alpha$1-Antitrypsin by a Monoclonal Antibody" Journal of Biological Chemistry, May 12, 2002, vol. 277, No. 29, pp. 26540-26546.
Taharaguchi S. et al., "Detection of an isoform of $\alpha_1$-antitrypsin in serum samples from foals with gastric ulcers", The Veterinary Record, Sep. 8, 2007, vol. 161, No. 10 pp. 338-342.
Kurachi K. et al., "Cloning and sequence of cDNA coding for $\alpha_1$-antitrypsin" Proc Natl Acad Sci USA, Nov. 1981, vol. 78, No. 11, pp. 6826-6830.
Yun-Ju Huang, "Studies of differential expressions of serum proteins in patients with endometriosis using proteomic approaches", Thesis. Taipei Medical University, Graduate Institute of Biomedical Material, 2005, pp. 1-102, English portions only.

* cited by examiner

*Primary Examiner* — Gary W Counts
(74) *Attorney, Agent, or Firm* — Muncy, Geissler, Olds & Lowe, P.C.

(57) ABSTRACT

Provided herein are monoclonal antibodies with a high binding affinity to isoforms of alpha 1-antitrypsin (A1AT), hybridoma cells producing the same, and their uses in diagnosing and/or detecting endometriosis from a serum sample of a subject suspicious of having endometriosis or a subject under health examination.

10 Claims, 11 Drawing Sheets

SEQUENCE LISTING

<160> NUMBER OF SEQ ID NOS: 27

<210> SEQ ID NO 1
<211> LENGTH: 20
<212> TYPE: PRT
<213> ORGANISM: artificial sequence
<220> FEATURE:
<223> OTHER INFORMATION: synthetic peptide

<400> SEQUENCE: 1

Glu Asp Pro Gln Gly Asp Ala Ala Gln Lys Thr Asp Thr Ser His His
1               5                   10                  15

Asp Gln Asp His
            20

<210> SEQ ID NO 2
<211> LENGTH: 20
<212> TYPE: PRT
<213> ORGANISM: artificial sequence
<220> FEATURE:
<223> OTHER INFORMATION: synthetic peptide

<400> SEQUENCE: 2

His Asp Gln Asp His Pro Thr Phe Asn Lys Ile Thr Pro Asn Leu Ala
1               5                   10                  15

Glu Phe Ala Phe
            20

<210> SEQ ID NO 3
<211> LENGTH: 20
<212> TYPE: PRT
<213> ORGANISM: artificial sequence
<220> FEATURE:
<223> OTHER INFORMATION: synthetic peptide

<400> SEQUENCE: 3

Ala Glu Phe Ala Phe Ser Leu Tyr Arg Gln Leu Ala His Gln Ser Asn
1               5                   10                  15

Ser Thr Asn Ile
            20

<210> SEQ ID NO 4
<211> LENGTH: 20
<212> TYPE: PRT
<213> ORGANISM: artificial sequence
<220> FEATURE:
<223> OTHER INFORMATION: synthetic peptide

<400> SEQUENCE: 4

Asn Ser Thr Asn Ile Phe Phe Ser Pro Val Ser Ile Ala Thr Ala Phe
1               5                   10                  15

Ala Met Leu Ser
            20

<210> SEQ ID NO 5
<211> LENGTH: 20
<212> TYPE: PRT
<213> ORGANISM: artificial sequence
<220> FEATURE:
<223> OTHER INFORMATION: synthetic peptide

<400> SEQUENCE: 5

Phe Ala Met Leu Ser Leu Gly Thr Lys Ala Asp Thr His Asp Glu Ile
1               5                   10                  15

-continued

Leu Glu Gly Leu
        20

<210> SEQ ID NO 6
<211> LENGTH: 20
<212> TYPE: PRT
<213> ORGANISM: artificial sequence
<220> FEATURE:
<223> OTHER INFORMATION: synthetic peptide

<400> SEQUENCE: 6

Ile Leu Glu Gly Leu Asn Phe Asn Leu Thr Glu Ile Pro Glu Ala Gln
1               5                   10                  15

Ile His Glu Gly
        20

<210> SEQ ID NO 7
<211> LENGTH: 20
<212> TYPE: PRT
<213> ORGANISM: artificial sequence
<220> FEATURE:
<223> OTHER INFORMATION: synthetic peptide

<400> SEQUENCE: 7

Gln Ile His Glu Gly Phe Gln Glu Leu Leu Arg Thr Leu Asn Gln Pro
1               5                   10                  15

Asp Ser Gln Leu
        20

<210> SEQ ID NO 8
<211> LENGTH: 20
<212> TYPE: PRT
<213> ORGANISM: artificial sequence
<220> FEATURE:
<223> OTHER INFORMATION: synthetic peptide

<400> SEQUENCE: 8

Pro Asp Ser Gln Leu Gln Leu Thr Thr Gly Asn Gly Leu Phe Leu Ser
1               5                   10                  15

Glu Gly Leu Lys
        20

<210> SEQ ID NO 9
<211> LENGTH: 20
<212> TYPE: PRT
<213> ORGANISM: artificial sequence
<220> FEATURE:
<223> OTHER INFORMATION: synthetic peptide

<400> SEQUENCE: 9

Ser Glu Gly Leu Lys Leu Val Asp Lys Phe Leu Glu Asp Val Lys Lys
1               5                   10                  15

Leu Tyr His Ser
        20

<210> SEQ ID NO 10
<211> LENGTH: 20
<212> TYPE: PRT
<213> ORGANISM: artificial sequence
<220> FEATURE:
<223> OTHER INFORMATION: synthetic peptide

<400> SEQUENCE: 10

Lys Leu Tyr His Ser Glu Ala Phe Thr Val Asn Phe Gly Asp Thr Glu
1               5                   10                  15

Glu Ala Lys Lys
            20

<210> SEQ ID NO 11
<211> LENGTH: 20
<212> TYPE: PRT
<213> ORGANISM: artificial sequence
<220> FEATURE:
<223> OTHER INFORMATION: synthetic peptide

<400> SEQUENCE: 11

Glu Glu Ala Lys Lys Gln Ile Asn Asp Tyr Val Glu Lys Gly Thr Gln
1               5                   10                  15

Gly Lys Ile Val
            20

<210> SEQ ID NO 12
<211> LENGTH: 20
<212> TYPE: PRT
<213> ORGANISM: artificial sequence
<220> FEATURE:
<223> OTHER INFORMATION: synthetic peptide

<400> SEQUENCE: 12

Gln Gly Lys Ile Val Asp Leu Val Lys Glu Leu Asp Arg Asp Thr Val
1               5                   10                  15

Phe Ala Leu Val
            20

<210> SEQ ID NO 13
<211> LENGTH: 20
<212> TYPE: PRT
<213> ORGANISM: artificial sequence
<220> FEATURE:
<223> OTHER INFORMATION: synthetic peptide

<400> SEQUENCE: 13

Val Phe Ala Leu Val Asn Tyr Ile Phe Phe Lys Gly Lys Trp Glu Arg
1               5                   10                  15

Pro Phe Glu Val
            20

<210> SEQ ID NO 14
<211> LENGTH: 20
<212> TYPE: PRT
<213> ORGANISM: artificial sequence
<220> FEATURE:
<223> OTHER INFORMATION: synthetic peptide

<400> SEQUENCE: 14

Arg Pro Phe Glu Val Lys Asp Thr Glu Glu Asp Phe His Val Asp
1               5                   10                  15

Gln Val Thr Thr
            20

<210> SEQ ID NO 15
<211> LENGTH: 20
<212> TYPE: PRT
<213> ORGANISM: artificial sequence
<220> FEATURE:
<223> OTHER INFORMATION: synthetic peptide

<400> SEQUENCE: 15

Asp Gln Val Thr Thr Val Lys Val Pro Met Met Lys Arg Leu Gly Met

```
1               5                  10                  15
Phe Asn Ile Gln
        20

<210> SEQ ID NO 16
<211> LENGTH: 20
<212> TYPE: PRT
<213> ORGANISM: artificial sequence
<220> FEATURE:
<223> OTHER INFORMATION: synthetic peptide

<400> SEQUENCE: 16

Met Phe Asn Ile Gln His Cys Lys Lys Leu Ser Ser Trp Val Leu Leu
1               5                   10                  15

Met Lys Tyr Leu
        20

<210> SEQ ID NO 17
<211> LENGTH: 20
<212> TYPE: PRT
<213> ORGANISM: artificial sequence
<220> FEATURE:
<223> OTHER INFORMATION: synthetic peptide

<400> SEQUENCE: 17

Leu Met Lys Tyr Leu Gly Asn Ala Thr Ala Ile Phe Phe Leu Pro Asp
1               5                   10                  15

Glu Gly Lys Leu
        20

<210> SEQ ID NO 18
<211> LENGTH: 20
<212> TYPE: PRT
<213> ORGANISM: artificial sequence
<220> FEATURE:
<223> OTHER INFORMATION: synthetic peptide

<400> SEQUENCE: 18

Asp Glu Gly Lys Leu Gln His Leu Glu Asn Glu Leu Thr His Asp Ile
1               5                   10                  15

Ile Thr Lys Phe
        20

<210> SEQ ID NO 19
<211> LENGTH: 20
<212> TYPE: PRT
<213> ORGANISM: artificial sequence
<220> FEATURE:
<223> OTHER INFORMATION: synthetic peptide

<400> SEQUENCE: 19

Ile Ile Thr Lys Phe Leu Glu Asn Glu Asp Arg Arg Ser Ala Ser Leu
1               5                   10                  15

His Leu Pro Lys
        20

<210> SEQ ID NO 20
<211> LENGTH: 20
<212> TYPE: PRT
<213> ORGANISM: artificial sequence
<220> FEATURE:
<223> OTHER INFORMATION: synthetic peptide

<400> SEQUENCE: 20
```

```
Leu His Leu Pro Lys Leu Ser Ile Thr Gly Thr Tyr Asp Leu Lys Ser
1               5                   10                  15

Val Leu Gly Gln
            20
```

<210> SEQ ID NO 21
<211> LENGTH: 20
<212> TYPE: PRT
<213> ORGANISM: artificial sequence
<220> FEATURE:
<223> OTHER INFORMATION: synthetic peptide

<400> SEQUENCE: 21

```
Ser Val Leu Gly Gln Leu Gly Ile Thr Lys Val Phe Ser Asn Gly Ala
1               5                   10                  15

Asp Leu Ser Gly
            20
```

<210> SEQ ID NO 22
<211> LENGTH: 20
<212> TYPE: PRT
<213> ORGANISM: artificial sequence
<220> FEATURE:
<223> OTHER INFORMATION: synthetic peptide

<400> SEQUENCE: 22

```
Ala Asp Leu Ser Gly Val Thr Glu Glu Ala Pro Leu Lys Leu Ser Lys
1               5                   10                  15

Ala Val His Lys
            20
```

<210> SEQ ID NO 23
<211> LENGTH: 20
<212> TYPE: PRT
<213> ORGANISM: artificial sequence
<220> FEATURE:
<223> OTHER INFORMATION: synthetic peptide

<400> SEQUENCE: 23

```
Lys Ala Val His Lys Ala Val Leu Thr Ile Asp Glu Lys Gly Thr Glu
1               5                   10                  15

Ala Ala Gly Ala
            20
```

<210> SEQ ID NO 24
<211> LENGTH: 20
<212> TYPE: PRT
<213> ORGANISM: artificial sequence
<220> FEATURE:
<223> OTHER INFORMATION: synthetic peptide

<400> SEQUENCE: 24

```
Glu Ala Ala Gly Ala Met Phe Leu Glu Ala Ile Pro Met Ser Ile Pro
1               5                   10                  15

Pro Glu Val Lys
            20
```

<210> SEQ ID NO 25
<211> LENGTH: 20
<212> TYPE: PRT
<213> ORGANISM: artificial sequence
<220> FEATURE:
<223> OTHER INFORMATION: synthetic peptide

<400> SEQUENCE: 25

```
Pro Pro Glu Val Lys Phe Asn Lys Pro Phe Val Phe Leu Met Ile Glu
1               5                   10                  15

Gln Asn Thr Lys
            20

<210> SEQ ID NO 26
<211> LENGTH: 19
<212> TYPE: PRT
<213> ORGANISM: artificial sequence
<220> FEATURE:
<223> OTHER INFORMATION: synthetic peptide

<400> SEQUENCE: 26

Glu Gln Asn Thr Lys Ser Pro Leu Phe Met Gly Lys Val Val Asn Pro
1               5                   10                  15

Thr Gln Lys

<210> SEQ ID NO 27
<211> LENGTH: 10
<212> TYPE: PRT
<213> ORGANISM: artificial sequence
<220> FEATURE:
<223> OTHER INFORMATION: synthetic peptide

<400> SEQUENCE: 27

Ser Leu Tyr Arg Gln Leu Ala His Gln Ser
1               5                   10
```

US 9,229,012 B2

SPECIFIC A1AT MONOCLONAL ANTIBODIES FOR DETECTION OF ENDOMETRIOSIS

RELATED APPLICATIONS

This application is a continuation of International Application No. PCT/US12/21315, filed Jan. 13, 2012; which claims the benefit of U.S. Provisional Application Ser. No. 61/433,183, filed on Jan. 14, 2011.

BACKGROUND OF THE INVENTION

1. Field of the Invention

The present disclosure relates, in general, to the diagnosis and/or detection of endometriosis. More particularly, the present disclosure is directed to monoclonal antibodies against alpha 1-antitrypsin (A1AT), hybridoma cells producing the same and their uses in diagnosing and/or detecting endometriosis from a serum sample of a subject.

2. Description of Related Art

Endometriosis is a disease characterized by the presence of endometrial tissue at ectopic sites, such as glands and stroma cells of endometrium which should have grown inside the uterus, but grow at sites outsides the uterus while preserving the same physiological form of a normal endometrium.

Endometriosis is often not discovered until pain or fever occurred to a patient during menstrual period, which is then confirmed by physical inspecting abdominal cavity of the patient. Since symptoms of endometriosis are often overlooked by the patient, the diagnosis of endometriosis is often delayed, resulting more complicated situation. Despite several approaches for diagnosing endometriosis are available, however, they either have low acceptance rate by the patient or have limited sensitivity toward certain types of endometriosis. For example, laparoscopy may provide reliable diagnosis to endometriosis, yet its acceptance by patient is low due to the invasive procedures involved. Vaginal ultrasonic or nuclear resonance imaging (MRI) technique offers sensitive measurement to fibroid or chocolatecyst larger than 2 cm, yet it is not sensitive enough for detecting endometriosis. A serum biomarker, CA125, has been proposed for diagnosing endometriosis (Barbieri R. L., Fertil. Steril. 45: 767-769, 1986), however, its sensitivity to endometriosis is a low 15%.

U.S. Pat. No. 7,399,598 issued to Yang et al on Jul. 15, 2008 disclosed a method for diagnosing endometriosis among females aged 18 to 40 by detecting the level of alpha 1-antitrypsin (A1AT), and/or its fragments in the serum specimen. However, the detection was achieved by conventional immuno-blotting analysis. Therefore, there exists in this art a need of an improved means having enough sensitivity that allows for early detection of endometriosis in a reliable manner.

SUMMARY

As embodied and broadly described herein, disclosure herein features monoclonal antibodies against alpha 1-antitrypsin (A1AT), hybridoma cells producing the same and their uses in diagnosing and/or detecting endometriosis from a biological sample, such as a serum sample of a subject.

In one aspect, the present disclosure is directed to monoclonal antibodies that specifically bind to isoforms of A1AT.

According to another embodiment, monoclonal antibodies 2A7 and 2C8, respectively bind to AAT1 and AAT2 are provided. Both AAT1 and AAT2 are isoforms of A1AT, and respectively have a molecular weight of about 72 and 58 kDa in a biological sample of a subject. The monoclonal antibody 2A7 or 2C8 is recognized by an epitope of A1AT having an amino acid sequence at least 90% identical to SEQ ID No. 3; and preferably, the monoclonal antibody 2A7 or 2C8 is recognized by an epitope of A1AT having an amino acid sequence of SEQ ID NO: 27. The monoclonal antibodies 2A7 and 2C8 are respectively an IgG1.

According to preferred embodiments, the biological sample may be a biopsy sample, a whole blood sample, a plasma sample, a serum sample, a peritoneal fluid, or purified or filtered forms thereof.

In another aspect, the present disclosure provides hybridomas that produced the monoclonal antibodies as described above.

In still another aspect, the present disclosure provides uses of the monoclonal antibodies as described above, including methods and/or kits for detecting endometriosis from a biological sample of a subject.

According to one embodiment of the present disclosure, a method of diagnosing endometriosis using the monoclonal antibody of the present disclosure is provided. The method includes steps of: obtaining a biological sample of a subject; contacting the biological sample with a monoclonal antibody that is 2A7 or 2C8; and detecting the respective binding of the monoclonal antibody 2A7 or 2C8 with AAT1 and AAT2; wherein the monoclonal antibody 2A7 or 2C8 is recognized by an epitope of A1AT having an amino acid sequence of SEQ ID NO: 27, and AAT1 and AAT2 respectively have a molecular weight of about 72 and 58 kDa in the biological sample.

The biological sample is a biopsy sample, a whole blood sample, a plasma sample, a serum sample, a peritoneal fluid, or purified or filtered forms thereof. In a preferred example, the biological sample is the serum sample.

Also within the scope of the present disclosure are diagnostic kits for detecting endometriosis from a biological sample of a subject.

According to one embodiment, the kit includes at least one of the monoclonal antibodies of this invention, at least one agent suitable for detecting the respective binding of the monoclonal antibodies 2A7 or 2C8 with AAT1 and AAT2 in the biological sample of the subject; and a legend associated with the kit and indicating how to use the kit; wherein the monoclonal antibody 2A7 or 2C8 is recognized by an epitope of A1AT having an amino acid sequence at least 90% identical to SEQ ID NO: 3, and preferably, an amino acid sequence of SEQ ID NO: 27, and the A1AT isoforms AAT1 and AAT2 respectively have a molecular weight of about 72 and 58 kDa.

The details of one or more embodiments of the invention are set forth in the description below. Other features, objects, and advantages of the present invention will be apparent from the description, and from the claims.

BRIEF DESCRIPTION OF THE DRAWINGS

\The present description will be better understood from the following detailed description read in light of the accompanying drawings, wherein.

DETAILED DESCRIPTION OF PREFERRED EMBODIMENTS

Figure 1:
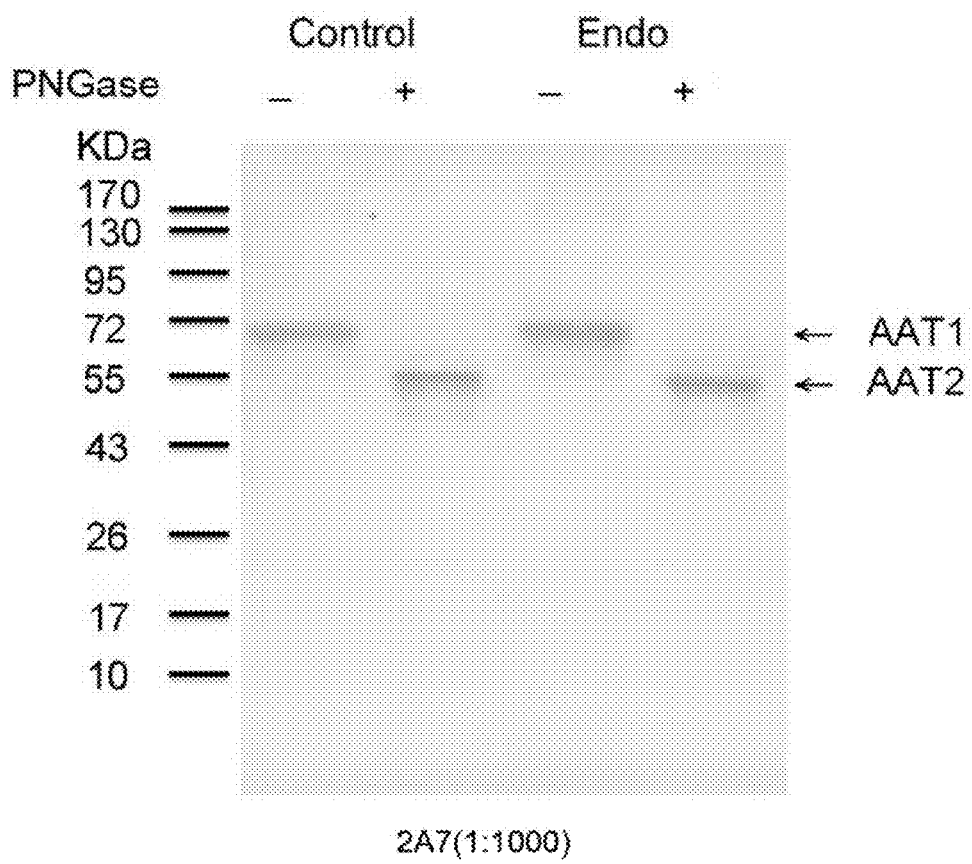
FIG. 1 illustrates the Western blot analysis of the A1AT isolated from healthy women or women having endometriosis, in which the A1AT has been pre-treated with or without a N-glycan digesting enzyme, PNGase F, in accordance with one embodiment of the present disclosure, in which C represents control, and Endo represents serum proteins from women having endometriosis.

The detailed description provided below in connection with the appended drawings is intended as a description of the present examples and is not intended to represent the only forms in which the present example may be constructed or utilized. The description sets forth the functions of the examples and the sequence of steps for constructing and operating the examples. However, the same or equivalent functions and sequences may be accomplished by different examples.

The terms "a", "an", and "the" as used herein are defined to mean "one or more" and include plural referents unless the context clearly dictates otherwise.

The term "antibody" or "antibodies" as used herein is art recognized term and is understood to refer to molecules or active fragments of molecules that bind to known antigens, particularly to immunoglobulin molecules and to immunological active portions of immunoglobulin molecules, i.e., molecules that contain a binding site that immune-specifically binds an antigen. The immunoglobulin according to this disclosure may be any type (e.g., IgG, IgM, IgD, IgE, IgA and IgY) or class (e.g., IgG1, IgG2, IgG3, IgG4, IgA1 and IgA2) or subclasses of immunoglobulin molecules.

The term "monoclonal antibody" is well recognized in the art and refers to an antibody that is mass produced in the laboratory from a single clone that recognizes only one antigen. Monoclonal antibodies are typically produced by fusing a normally short-lived, antibody-producing B cell to a fast-growing cell, such as an immortal cell. The resulting hybrid cell, or hybridoma, multiplies rapidly, creating a clone that produces large quantities of the antibody.

The practices of this invention are hereinafter described in detail with respect to monoclonal antibodies against alpha 1-antitrypsin (A1AT), hybridoma cells producing the same and their uses in diagnosing and/or detecting endometriosis from a biological sample, such as, a serum sample of a subject.

According to one aspect of the present disclosure, monoclonal antibodies that specifically bind to isoforms of A1AT are provided. According to one embodiment, the A1AT isoforms may be prepared by digesting A1AT with an endoglycosidase to remove N-glycan chains of the A1AT. Endoglycosidase is an enzyme that releases oligosaccharides from glycoproteins, or merely cleaves polysaccharide chains between residues that are not the terminal residue. Suitable endoglycosidase includes, but is not limited to, endoglycosidase D, F, F1, F2, G or H. In one example, PNGase F was used to release N-glycan chains from A1AT. According to one preferred embodiment, two isoforms of A1AT respectively having a molecular weight of about 72 and 58 kDa. The two isoforms of A1AT respectively having a molecular weight of about 72 kDa and 58 kDa are termed "AAT1" and "AAT2" hereafter, and are used as antigens for binding monoclonal antibodies against A1AT, or for detecting and/or diagnosing endometriosis from a biological sample of a subject.

To produce the desired monoclonal antibodies, animals such as mice, rats or rabbits are first immunized with A1AT at a suitable dose. Generally, adjuvant and the A1AT solution are mixed together when immunizing the animals with A1AT. Examples of adjuvants useful for this invention include Freund's complete adjuvant (FCA), Freund's incomplete adjuvant (FIA), and aluminum hydroxide adjuvant. Immunization is generally carried out mainly by intravenous, subcutaneous, intraperitoneal or intramuscular injection of the antigen. The immunization interval is not particularly limited. Immunization may be carried out at intervals of several days to several weeks, preferably 2 to 3 weeks, for 1 to 10 times, preferably 2 to 5 times. Once antibody titers reaches 2 or more in the absorbance level as the result of immunization, the animals are left for 2 to 6 months, preferably 4 to 6 months, more preferably 6 months, until the antibody titers have decreased to 0.05-1, preferably 0.05-0.5, more preferably 0.05, in the absorbance level.

Then, re-immunization is carried out for a plurality of times, preferably 2 to 5 times, at intervals of several weeks. Several days, preferably 3 to 5 days, after the final immunization, splenic cells and regional lymph nodes are removed. Blood samples are taken regularly after immunization and subject to centrifugation to separate sera. The resultant sera are then subject to measurement of antibody titers by any suitable method, which includes, and is not limited to, enzyme linked immunosorbent assay (ELISA), enzyme immunoassay (EIA), or radio immunoassay (RIA). In one preferred example, antibody titers are measured by ELISA. Then, final immunization is given to those animals showing high antibody titers to MAT isoforms prepared by steps described above.

Antibody-producing cells are prepared from splenic cells and regional lymph nodes or the like of the immunized animals. In the preparation of antibody-producing cells, it is preferably to remove tissue debris and erythrocytes as much as possible. Commercial erythrocyte remover may be used to this purpose. Alternatively, a buffer ammonium chloride and Tris may be prepared and used.

The thus prepared antibody-producing cells should be immediately fused with immortal cells such as myeloma cells to produce hybridoma cells, which semi-eternally continue to proliferate while producing antibodies. Commonly available cell strain derived from an animal such as mouse may be used. A preferable cell strain to be used in this invention should not survive in HAT selection medium, which contains hypoxanthine, thymidine and aminopterin, and should survive there only when fused with antibody-producing cells. Examples of myeloma cells include, but are not limited to, mouse myeloma cell line (such as myeloma FO cells) and human myeloma cell line (such as Karpas 707H).

Cell fusion is usually carried out by mixing splenic cells or lymph node cells with a commercial available myeloma cells in the presence of a cell-fusion promoter, such as polyethylene glycol (PEG) having an average molecular weight from about 200 to 20,000 daltons or the like. Alternatively, cell fusion may be carried out in a commercial cell fusion device utilizing electric stimulation such as electroporation. After the fusion, the resultant cells are then diluted and cultured in HAT medium.

Hybridomas of interest are then selected from the fused cells. The fused cells surviving cultured in HAT medium would form colonies. The supernatant of each culture well is then collected and examine for the presence or absence of antibody titers to AAT1 or AAT2 (i.e., isoforms of A1AT prepared by steps described above). As a method of confirmation, ELISA, EIA or RIA may be used. Once antibody-positive wells are identified, cells are then cultured in a HT medium, which does not contain aminopterin. After culturing for a while, antibody titers in the culture supernatant are confirmed again. Cells that are finally selected are then subject to cloning to obtain single cells. Clones that exhibit high specificity to AAT1 or AAT2 are selected, and are proliferated to some extent to establish hybridomas.

According to preferred embodiments of the present disclosure, three hybridomas were selected. The two hybridomas, respectively produce monoclonal antibodies 2A7 and 2C8, which respectively bind to AAT1 and AAT2.

The thus produced monoclonal antibodies may be isolated or prepared by any known method. For example, antibodies may be prepared from cultured supernatant obtained by culturing hybridomas in a medium with low serum concentration. Alternatively, hybridomas may be injected into abdominal cavities of animals and the resultant abdominal dropsies are collected to prepare antibodies. Antibodies may be purified or isolated by methods that employ affinity column, gel filtration chromatography, ion exchange chromatography or the like. Any of these known methods may be appropriately selected or used in combination.

According to one embodiment of the present disclosure, the monoclonal antibody produced by the selected strain and specifically binds to AAT1 (i.e., an A1AT isoform having a molecular weight of about 72 kDa). The thus produced monoclonal antibody is an IgG1 and is termed "2A7" hereafter.

According to another embodiment of the present disclosure, the monoclonal antibody produced by the selected strain and specifically binds to AAT2 (i.e., an A1AT isoform having a molecular weight of about 58 kDa). The thus produced monoclonal antibody is an IgG1 and is termed "2C8" hereafter.

Since AAT1 and AAT2 may be used as biomarkers for detecting and/or diagnosing endometriosis of a subject; the monoclonal antibodies of the present disclosure may thus be used in a method or assembled into kits, to detect endometriosis from a biological sample, such as, a serum sample or a smear sample, of the subject.

According to one embodiment of this invention, it is possible to detect endometriosis by reacting any of the monoclonal antibodies with a biological sample to thereby measure any A1AT isoforms (i.e., AAT1 or AAT2) in the biological sample and using the measured result as an indicator. The measurement may be performed by any of the conventional immunoassays and is not particularly limited.

For this purpose, biological sample are taken from subjects suspicious of endometriosis or subjects of health examination. The biological sample may be any of a smear sample, a biopsy sample, a whole blood sample, a plasma sample, a serum sample, a urine sample, a peritoneal fluid, or purified or filtered forms thereof. From the view point of early detection, blood, serum, or plasma sample is preferred. The thus prepared biological samples are then reacted with any of the monoclonal antibodies of this disclosure. Measurement of endometriosis or measurement of AAT1 and AAT2 level in the biological sample may be performed by conventional ELISA or dot-blot analysis.

According to another embodiment of the present disclosure, it is possible to use the monoclonal antibody against any A1AT isoforms such as AAT1 or AAT2 in an endometriosis detection kit or as a reagent for AAT1 or AAT2 detection.

The inventors have thus contemplated an AAT1 or AAT2 detection kit, which is capable of measuring respective level of AAT1 and AAT2 in a biological sample with high sensitivity. The kit of the present invention includes at least one of the monoclonal antibodies selected from the group consisting of 2A7 and 2C8; at least one agent suitable for detecting the respective binding of 2A7 and 2C8 with AAT1 and AAT2 in the biological sample of the subject; and a legend associated with the kit and indicating how to use the kit. The biological sample described herein includes, but is not limited to, a biopsy sample, a whole blood sample, a serum sample, a plasma sample, and purified or filtered forms thereof. The components included in the kits are: a container; the monoclonal antibodies 2A7 or 2C8; reagents for detecting a biological sample; and a legend associated with the container and indicating how to use the monoclonal antibodies for detecting A1AT in the biological sample. The legend may be in a form of pamphlet, tape, CD, VCD or DVD. The kit may further comprise a negative control that indicates the normal level of A1AT in a subject.

To determine the epitope(s) of A1AT recognized by the monoclonal antibody 2A7 or 2C8 of this invention, the full length of A1AT mature polypeptide having 418 amino acids in length is divided into 26 fragments consecutively, with overlapping amino acid residues in each fragment. Each peptide fragment contains about 20 amino acid residues of human A1AT. The A1AT-derived peptide may be synthesized in accordance with any standard peptide synthesis protocol in the art. In one embodiment, the A1AT-derived peptides were synthesized by use of a solid-phase peptide synthesizer (ABI433A peptide synthesizer, Applied Biosystems Inc., Life Technologies Corp., Foster City, Calif., USA) in accordance with the manufacturer's protocols. The synthetic peptides were designated as P-1 (SEQ ID NO: 1), P-2 (SEQ ID NO: 2), P-3 (SEQ ID NO: 3), P-4 (SEQ ID NO: 4), P-5 (SEQ ID NO: 5), P-6 (SEQ ID NO: 6), P-7 (SEQ ID NO: 7), P-8 (SEQ ID NO: 8), P-9 (SEQ ID NO: 9), P-10 (SEQ ID NO: 10), P-11 (SEQ ID NO: 11), P-12 (SEQ ID NO: 12), P-13 (SEQ ID NO: 13), P-14 (SEQ ID NO: 14), P-15 (SEQ ID NO: 15), P-16 (SEQ ID NO: 16), P-17 (SEQ ID NO: 17), P-18 (SEQ ID NO: 18), P-19 (SEQ ID NO: 19), P-20 (SEQ ID NO: 20), P-21 (SEQ ID NO: 21), P-22 (SEQ ID NO: 22), P-23 (SEQ ID NO: 23), P-24 (SEQ ID NO: 24), P-25 (SEQ ID NO: 25) and P-26 (SEQ ID NO: 26); and are described in detail in Table 1 in one preferred example.

Any skilled person in this art may modify the synthesized peptides by methods (such as a computer simulation program) that predict the effect on polypeptide conformation of a change in polypeptide sequence, and thus may "design" or "modify" a A1AT-derived peptide based on the information disclosed herein by proposing and testing a modified A1AT-derived peptide to determine whether the modified A1AT-derived peptide retains a desired function or conformation. The A1AT-derived peptide may be modified specifically to alter a feature of the peptide unrelated to its physiological activity. For example, cystein residues can be substituted or deleted to prevent unwanted disulfide linkage. Similarly, certain amino acids can be changed and/or deleted without affecting the physiological activity of the peptide in this study (i.e., its ability to bind to 2A7 or 2C8 monoclonal antibody in an immunoassay). This invention thus encompasses functionally equivalent derivatives of A1AT-derived peptides synthesized in one embodiment of this invention, including peptides having conservative amino acid substitutions. Conservative substitutions of amino acids include substitutions made amongst amino acids within the following groups: (a) M, I, L, V; (b) F, Y, W; (c) K, R, H; (d): A, G; (e) S, T; (f) Q, N; (g) E, D; and (h) C, M.

According to one specific embodiment of this invention, the A1AT-derived peptides and full length A1AT are subject to competitive binding with the monoclonal antibody 2A7 or 2C8, so as to determine the A1AT-derived peptide (i.e., A1AT epitope) that may be recognized by the monoclonal antibody of this invention. Antibody binding may be detected by techniques known in the art, such as radioimmunoassay, enzyme-linked immunosorbent assay (ELISA), "sandwich" immunoassay, in situ immunoassays (e.g., using colloidal gold, enzyme or radioisotope labels), western blot, agglutination assay (e.g., gel agglutination assay, hemagglutination assay and etc), complement fixation assay, immunofluorescence assay, and immunoelectrophoresis assay and etc. In one embodiment, antibody binding is detected by use of ELISA. Both monoclonal antibodies 2A7 and 2C8 are recognized by the A1AT-derived peptide, particularly, the synthetic A1AT peptide P-3 (SEQ ID NO: 3).

Preferably, the synthetic A1AT peptide comprises an amino acid sequence at least 90% identical to SEQ ID NO: 3.

More preferably, the synthetic A1AT peptide comprises an amino acid sequence at least 90%, 91%, 92%, 93%, 94%, 95%, 96%, 97%, 98%, 99% or 100% identical to SEQ ID NO: 3. In a most preferred example, the synthesized A1AT peptide has an amino acid sequence of SEQ ID NO: 27. Percentage of identity is a measure of the number of identical amino acid residues in an uninterrupted linear sequence of a polypeptide when compared to a target polypeptide sequence of specified length. As used herein, "identity" of a sequence means that the compared amino acid residues in two separate sequences are identical. Thus, 100% identity means, for example, that upon comparing 20 sequential amino acid residues in two different molecules, both 20 residues in the two different molecules are identical.

The following examples are provided to illustrate the present invention without, however, limiting the same thereto.

EXAMPLES

The monoclonal antibodies (mAbs), hybridomas for producing the mAbs and uses thereof of the present disclosure will be illustrated in further detail with reference to several examples below, which are not intended to limit the scope of the present disclosure.

Example 1

Preparation of Antigens

Serum samples were obtained with informed consent from women having endometriosis. The serum samples were precipitated by adding 4 times volume of cold acetone containing 10% (w/v) trichloracetic acid (TCA). The mixture was kept at −20° C. for 90 min, then centrifuged at 4° C. with a speed of 15,000×g for 20 min. The pellet was collected and washed with ice-cold acetone, followed by another centrifugation at a speed of 15,000×g for 20 min. The supernatant was discarded, and the pellet was dissolved in rehydration buffer (7M urea, 4% CHAPS ([3-(3-cholamidopropyl)dimethylammonio]-1-propanesulfonate), 2M thiourea, 0.002% bromophenol blue, and 65 mM dithioerythritol (DTE)).

The proteins in the rehydration buffer were subsequently treated with PNGase F to remove any N-glycan chains of the proteins. The digested proteins were then identified by Western blot. Briefly, equal amount of protein samples were electrophoresized with 10% SDS-PAGE and then transferred to a PVDF membrane (Minipore) using Bio-Rad semi-dry system. Non-specific binding was blocked by 5% skim milk in TBS buffer (20 mM Tris-base, 0.5M NaCl, and pH 8.0) for an hour, the blot was then incubated with anti-human α1-antitrypsin antibody (i.e., AAT704 antibody, Santa Cruz Biotechnology, Inc., Santa Cruz, Calif.) in TBS with 0.1% skim milk at 4° C. overnight. After three 10-min washes with TBST buffer (TBS buffer containing 0.1% Tween-20), the blot was soaked in a solution containing an alkaline phosphatase-conjugated goat anti-mouse IgG secondary antibody or horse radish peroxidase (HRP)-conjugated goat anti-mouse IgG antibody in an appropriate dilution in TBS with 0.1% skin mile for 1 hour at room temperature. After extensive washing with TBST buffer and TBS buffer for 10 min, the blot was incubated with NBT/BCIP that interacted with AP or DAB/$H_2O_2$ that interacted with HRP for colorimetric development. Result is illustrated in FIG. 1.

FIG. 1 depicts the Western blot analysis of the protein antigens isolated from women having endometriosis in the presence or absence of a N-glycan digesting enzyme, PNGase F, which removes any N-glycan chains of the proteins. Two isoforms of A1AT protein bands at 72 and 58 kDa were identified and respectively termed AAT1 and AAT2.

Example 2

Production of Monoclonal Antibodies 2.1 Immunization the Animals with Alpha 1-Antitrypsin (A1AT) and Measurement of Antibody Titers Mice were immunized with alpha 1-antitrypsin (A1AT, purchased from Sigma Inc) at a dose of 30 μg/animal, 2 to 6 times, in 4 week intervals. After 2 boosting, the blood samples were taken every week, and were immediately centrifuged to separate sera. The resultant sera were subjected to serial dilution, followed by measurement of antibody titers by Western blot 2.2 Preparation of Antibody-Producing Cells Animals with desired titers in example 2.1 (i.e., when a 1:5,000 dilution of the sera were positive in western blot) were selected for a fusion. Antibody-producing cells were prepared from splenic cells, regional lymph nodes of the immunized animals, and hybridomas were generated by fusion the antibody-producing cells with a myeloma FO cell line in accordance with the procedures described by Hong et al (J Immunol Methods 120: 151-157 (1989)). Briefly, $1\times10^6$ cells/ml of splenic cells or lymph node cells were mixed with $2\times10^6$ cells/ml of myeloma cells in serum free PMI-1640 medium in the presence of polyethylene glycol (PEG), which has a molecular weight of about 1,500 Da. After fusion, the resulted hybrid cells were then cloned in the conventional manner, such as using limited dilution.

2.3 Establishment of Hybridomas 10-14 days after the cell fusion, allowed the cells selected in accordance with steps described in example 2.2 to form colonies. The supernatant in each colony-positive well of the culture plate was collected, and examined for the presence or absence of antibody titers to AAT1 or AAT2 of Example 1 by ELISA. Once antibody-positive wells were confirmed, cells were transferred to 24-well or 12-well plates and the medium was replaced with HT medium (i.e., HAT (hypoxanthine, aminopterin and thymidine) medium that does not contain aminopterin).

Cells in finally selected wells were then subjected to cloning to obtain single cells. Briefly, cell suspensions is diluted with 20% FCS-containing RPMI 1640 medium and seeded in 96-well plates at about 0.5-2 cells/well. The smaller the number of cells seeded in each well of the 96-well plate, the higher the probability the one cell is seeded in one well. 7-10 days after seeding, collect the supernatant of the culture plates and tested for its antibody titers. Again, clones having high specificity to AAT1 or AAT2 and low cross-reactivity to AAT1 or AAT2 analogs were selected, and proliferated to some extent to form hybridomas. In sum, three clones that produced the desired monoclonal antibodies were selected and cultured, in which two clones produced antibodies that specifically bound to AAT2 with high affinity; and one clone produced antibodies that specifically bound to AAT1 with high affinity.

2.4 Production of Monoclonal Antibodies

AAT1 or AAT2 specific monoclonal antibodies were purified and prepared from the established hybridomas of Example 2.3 by the method described below. Approximately $10^6$ to $10^7$ hybridoma cells were administered to the abdominal cavity of a mouse to expand the hybridoma cells. After 1 to 2 weeks, the abdominal dropsy from each mouse was then harvested to collect monoclonal antibodies. The obtained IgG is prepared by $(NH_4)_2SO_4$ precipitation followed by protein G purification.

The monoclonal antibodies thus produced with high affinity to AAT1 and AAT2, respectively were IgG1 isotype and were respectively termed 2C8 and 2A7.

Example 3

The Detection of Endometriosis Using Monoclonal Antibodies of Example 2

The specificity of the monoclonal antibodies 2A7 and 2C8 of Example 2 was analyzed using immune-dot blot analysis.

In this example, serum samples from total of 235 women were obtained with informed consent, and were classified into 5 groups. The control group was composed of 48 women without endometriosis at reproducing age. 89 women with mild (or early) stage pelvic endometriosis and whom had not received gonadotropin-releasing hormone (GnRh) treatment were classified as Ecdo(+)GnRh(−) I/II group. 16 women with severe stage of pelvic endometriosis and whom had not received GnRh treatment were classified as Ecdo(+)GnRh(−) III/IV group. 23 women with adenomyosis were classified as Adenomyosis group. Finally, 59 women with pelvic endometriosis and whom have received GnRh treatment were classified as Endo(+)GnRh(+) group.

To perform dot-blot analysis; 5 ng of serum collected from women described above were blotted onto a PVDF membrane. After blocking with 5% skimmed milk at 4° C. for overnight, PVDF membrane was incubated with mouse monoclonal anti-A1AT antibody (2A7 or 2C8 of Example 2) (1:1000 dilution) at room temperature for 1 hour. After extensive washes with TBST buffer, DAB solution (10 ml PBS, 0.5 ml $NiCl_2$, 10 μl $H_2O_2$, and 0.2 mg DAB powder) containing chromogen was added for color development. The reacted dot intensity, which represents the level of A1AT detected by the indicated A1AT antibody. Various amount of A1AT were also blotted onto the membrane as the internal control. The dot intensity was quantified using image processing software (Scion, USA). Results are illustrated in FIG. 2.

Figure 2:
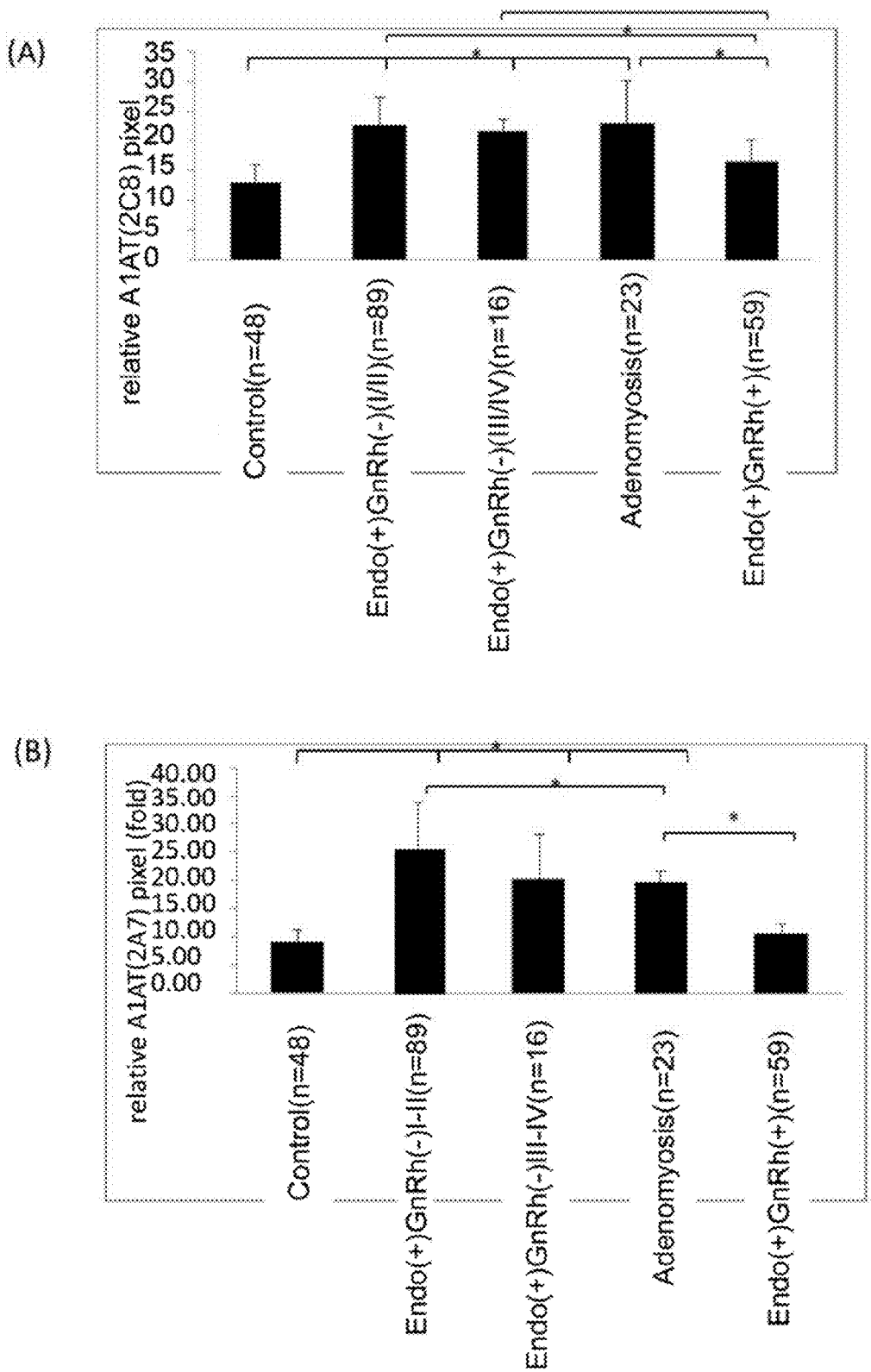
FIG. 2 illustrates the quantitatively measurement of the dot intensity representing the expression of A1AT as measured in subjects by immune dot blot analysis using (A) 2C8 or (B) 2A7 monoclonal antibody of Example 2, subjects were classified into 5 different groups, in which control represents 28 women without endometriosis; Endo(+)GnRh(−)I-II represents 89 women having mild stage of endometriosis; Endo(+)GnRh(−)III-IV represents 16 women having severe stage of endometriosis; Adenomyosis represents 23 women having endometriosis that migrate to peritoneum; and Endo(+)GnRh(+) represents 59 women having endometriosis and have been treated with GnRh, *represents statistically significant (P-value<0.05)

As depicted in FIG. 2, significant levels of A1AT isotypes were observed in women having mild or sever stage endometriosis, as well as in women having adenomyosis. The presence of A1AT isotypes were detected and recognized by the monoclonal antibodies 2C8 (FIG. 2A) and 2A7 (FIG. 2B) raised in accordance with the procedures described in Example 2.

Figure 3:
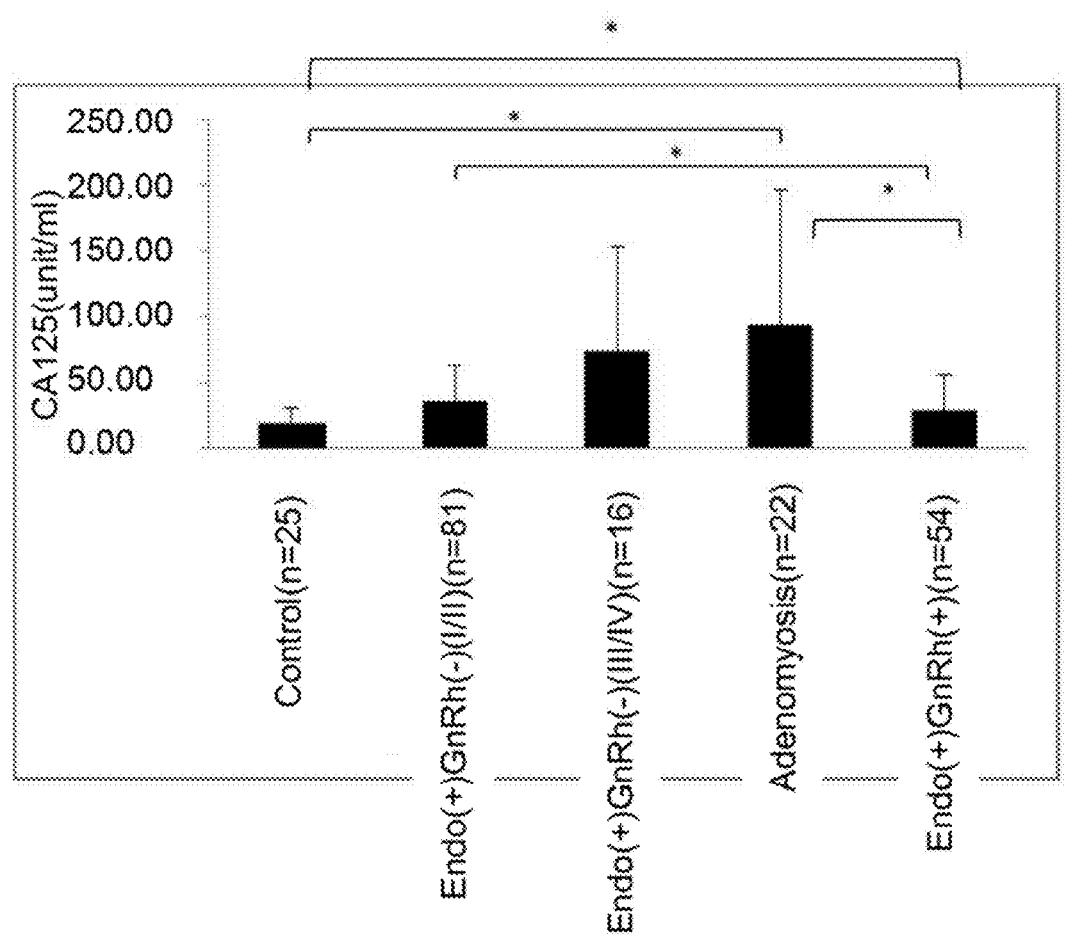
FIG. 3 illustrates the quantitatively measurement of the dot intensity representing the expression of A1AT as measured in subjects by immune dot blot analysis using CA125 as an indicator, in which control represents 25 women without endometriosis; Endo(+)GnRh(−)I-II represents 81 women having mild stage of endometriosis; Endo(+)GnRh(−)III-IV represents 16 women having severe stage of endometriosis; Adenomyosis represents 22 women having endometriosis that migrate to peritoneum; and Endo(+)GnRh(+) represents 54 women having endometriosis and have been treated with GnRh. *represents statistically significant (P-value<0.05)

As a comparison, another biomarker, CA125, was tested to see if it was useful for the detection of endometriosis. As depicted in FIG. 3, although women having severe stage endometriosis or adenomyosis exhibited high level of CA125, yet the amount of CA125 in women having mild stage endometriosis is not significantly different from any of the control, women having mild stage endometriosis or women having pelvic endometriosis and also received GnRh treatment. The results suggest that, compared to monoclonal antibodies of this invention, CA125 is a poor biomarker in terms of detecting endometriosis.

Example 4

Comparative Study on Detection Efficiency Between Monoclonal Antibodies of Example 2, CA125 and Known A1AT Antibody To verify the sensitivity, specificity and/or accuracy of monoclonal antibodies of Example 2 in the early detection of endometriosis, they were subject to binding test as described in Example 3, in comparison with CA125 and another commercial available anti-A1AT antibody (i.e., AAT704, obtained from Santa Cruz Biotechnology, Inc., Santa Cruz, Calif., USA).

Blood samples were taken with informed consent from 48 women, which were further classified into 4 groups according to their respective disease stages, in which control represents 8 healthy women at reproductive age; Endo (I/11) represents 89 women having mild (stage I or II) endometrosis; Endo (III/IV) represents 16 women having severe (stage III or IV) endometrosis; and AP represents 50 women having adenomyosis.

Sensitivity and specificity of each antibody for detecting endometriosis antigen, AAT1 or AAT2 of Example 1, in the serum sample was calculated based on the cut-off level determination from receiver operation characteristic (ROC) of each do-blot assay. The area under the curve was approximately the percentage correctly classified. Cut-off point on ROC curve was determined by the minimal value for $(1-\text{sensitivity})^2+(1-\text{specificity})^2$.

Table I summarizes the sensitivity, specificity and accuracy of the indicated antibodies, monoclonal antibodies of Example 2, CA125 or AAT704, in diagnosing or detecting the presence of endometriosis antigen in serum samples obtained from women described above.

The overall sensitivity of monoclonal antibodies of Example 2 for detecting endometriosis in all stages was much higher than that by AAT704 or CA125. With respect to the sensitivity, 2C8 and 2A7 antibodies of the present invention in all stages was over 90%; whereas CA125 exhibited a low 20% sensitivity for early stage endometriosis, which then increased to about 68% for severe stage endometriosis. AAT704, on the other hand, was more sensitive toward early stage endometriosis (over 70%), than severe stage endometriosis (about 13%). With respect to specificity, 2C8 and 2A7 both exhibited a specificity at least 93% to all stages endometriosis; whereas specificity for CA125 and AAT704 were about 92% and 50-90%, respectively.

sured by immune dot blot assay in accordance with the steps described in Example 3. Results are illustrated in FIG. 4.

Figure 4A:
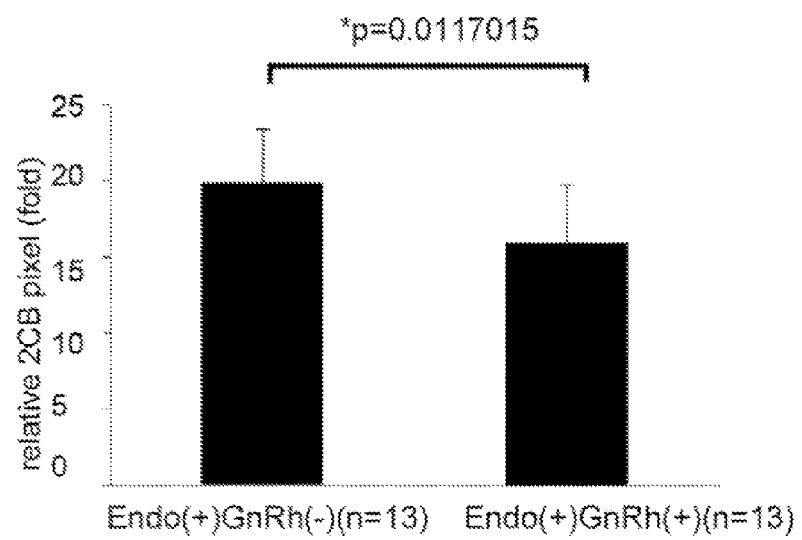
FIGS. 4A and 4B illustrate the level of AAT2 respectively detected by monoclonal antibodies 2C8 (A) and 2A7 (B) in serum samples collected from endometriosis women treated with GnRh.
Figure 4B:
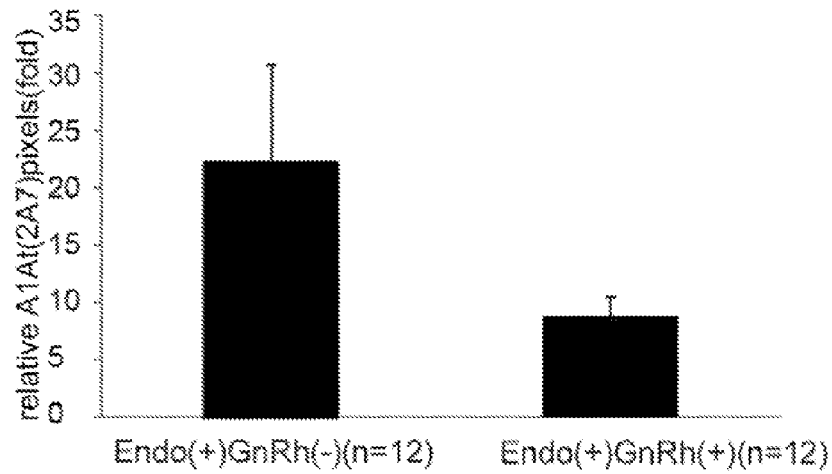

It is clear from FIGS. 4A and 4B that the levels of AAT2 in endometriosis women after receiving GnRh treatment, either detected by monoclonal antibody 2C8 or 2A7 of Example 2, drops significantly, as compared with those of endometriosis women without GnRh treatment.

Figure 4C:
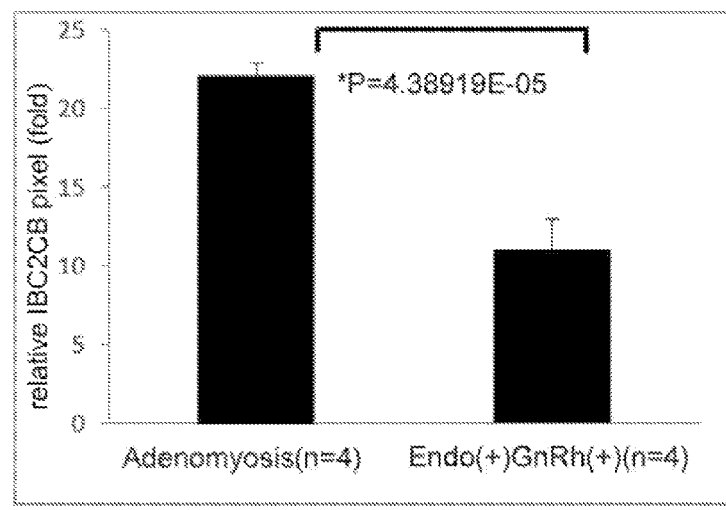
FIG. 4C illustrates the level of AAT2 detected by monoclonal antibody 2C8 in serum samples collected from adenomyosis women treated with GnRh.

Similar results were also found in women having adenomyosis, after receiving GnRh treatment, the serum levels of AAT2 in these women as detected by monoclonal antibody 2C8, decreased significantly, as compared with those without GnRh treatment (FIG. 4C).

The finding in this example confirms that at least AAT2, the A1AT isoform having a molecular weight of 58 kDa identified in the present study, is a good biomarker for the occurrence of endometriosis, and may be effectively detected by the monoclonal antibody 2C8 or 2A7 of the present disclosure.

Example 6

Epitope Mapping of Monoclonal Antibodies of Example 2

6.1 Preparation of Synthetic A1AT Peptides

In order to define the A1AT epitope(s) recognized by monoclonal antibodies of Example 2, A1AT was divided into 26 fragments of peptides, which were prepared by use of an automatic solid-phase peptide synthesizer (ABI433A peptide synthesizer, Applied Biosystems Inc., Life Technologies Corp., Foster City, Calif., USA). Standard procedures of $N^\alpha$-9-fluorenylmethoxycarbonyl (Fmoc) chemistry were used to prepare these peptides. The primary sequence of each peptide is provided in TABLE 2.

All synthetic A1AT peptides were purified by reversed-phase high performance liquid chromatography (RP-HPLC) with a semi-preparative octadecyl ($C_{18}$) column. The mobile

TABLE 1

| Abs | Disease stage | Cut off (U) | AUC | P-value* | Sensitivity | Specificity | Accuracy |
|---|---|---|---|---|---|---|---|
| CA125 | I, II | 35 | 0.926 | 4.87335E−06 | 20.99 | 92.00 | 37.74 |
| CA125 | III, IV | 35 | 0.785 | 0.016643999 | 68.75 | 92.00 | 82.93 |
| A1AT(2C8) | I, II | 17.158 | 0.967 | 2.06496E−19 | 86.52 | 93.75 | 89.78 |
| A1AT(2C8) | III, IV | 17.217 | 0.977 | 1.39022E−08 | 93.75 | 93.75 | 93.75 |
| A1AT(2A7) | I, II | 15.454 | 1 | 5.58569E−22 | 94.38 | 100.00 | 100 |
| A1AT(2A7) | III, IV | 13.473 | 0.992 | 4.61083E−09 | 93.75 | 95.83 | 95.31 |
| AAT704 | I, II | 0.899 | 0.899 | 7.86079E−09 | 74.67 | 91.30 | 79.59 |
| AAT704 | III, IV | 0.055 | 0.055 | 3.45168E−05 | 13.04 | 52.17 | 64.70 |

*A P-value with p < 0.05 indicates that the differences between each group is significant.

Example 5

The Level of MAT Isoforms Detected by Monoclonal Antibodies of Example 2 in Serum Samples Collected From Endometriosis Women Treated with GnRh In this example, monoclonal antibodies of Example 2, 2C8 and 2A7, were used to detect the level of AAT2 in serum samples collected from endometriosis women after being treated with GnRh, so as to confirm that A1AT isoforms of Example 1 are indeed good indicators for the occurrence of endometriosis. The binding of the respective monoclonal antibodies with a corresponding A1AT isoform were meaphase in the RP-HPLC is acetonitrile/water solvent system containing 0.1% trifluoroacetic acid (TFA). Detection was made at a wavelength of 220 nm and peaks were recorded and quantified. Eluate from each run of purification was collected and fractions with identical components were pooled together and then recovered by lyophilization in vacuum condition. The final purity of each collected peptide was determined by analytical RP-HPLC and 95% or higher in purity was achieved. The synthetic peptides were kept frozen at −20° C. until used.

The purified A1AT synthetic peptides were further characterized for their molecular weights by electrospray ionization mass spectroscopy (ESI-MS).

TABLE 2

The synthetic A1AT peptides

| Peptide Number | Residue No. in A1AT | Amino Acid Sequence | SEQ ID No |
|---|---|---|---|
| 1 | 25-44 | H₂N-EDPQGDAAQKTDTSHHDQDH-COOH | 1 |
| 2 | 39-59 | H₂N-HDQDHPTFNKLTPNLAEFAF-COOH | 2 |
| 3 | 55-74 | H₂N-AEFAFSLYRQLAHQSNSTNI-COOH | 3 |
| 4 | 70-99 | H₂N-NSTNIFFSPVSIATAFAMLS-COOH | 4 |
| 5 | 86-105 | H₂N-FAMLSLGTKADTHDEILEGL-COOH | 5 |
| 6 | 101-120 | H₂N-ILEGLNFNLTELPEAQLHEG-COOH | 6 |
| 7 | 116-135 | H₂N-QIHEGFQELLRTLNQPDSQL-COOH | 7 |
| 8 | 131-150 | H₂N-PDSQLQLTTGNGLFLSEGLK-COOH | 8 |
| 9 | 146-165 | H₂N-SEGLKLVDKFLEDVKKLYHS-COOH | 9 |
| 10 | 161-180 | H₂N-KLYHSEAFTVNFGDTEEAKK-COOH | 10 |
| 11 | 176-195 | H₂N-EEAKKQINDYVEKGTQGKIV-COOH | 11 |
| 12 | 191-210 | H₂N-QGKIVDLVKELDRDTVFALV-COOH | 12 |
| 13 | 206-215 | H₂N-VFALVNYIFFKGKWERPFEV-COOH | 13 |
| 14 | 221-240 | H₂N-RPFEVKDTEEEDFHVDEQVTT-COOH | 14 |
| 15 | 236-255 | H₂N-DQVTTVKVPMMKLGMFNIQ-COOH | 15 |
| 16 | 251-270 | H₂N-MFNIQHCKKLSSWVLLMSKYL-COOH | 16 |
| 17 | 266-285 | H₂N-LMKYLGNATAIFFLPDEGKL-COOH | 17 |
| 18 | 281-300 | H₂N-DEGKLQHLENELTHDIITKF-COOH | 18 |
| 19 | 296-315 | H₂N-IITKFLENEDRRSASLHLPK-COOH | 19 |
| 20 | 311-330 | H₂N-LHLPKLSITGTYDLKSVLGQ-COOH | 20 |
| 21 | 326-345 | H₂N-SVLGQLGITVFSNGADLSG-COOH | 21 |
| 22 | 341-360 | H₂N-ADLSGVTEEAPLKLSKAVHK-COOH | 22 |
| 23 | 356-375 | H₂N-KAVHKAVLTIDEKGTEAAGA-COOH | 23 |
| 24 | 371-395 | H₂N-EAAGAMFLEAIPMSIPPEVK-COOH | 24 |
| 25 | 391-405 | H₂N-PPEVKFNKPFVFLMIEQNTK-COOH | 25 |
| 26 | 401-418 | H₂N-EQNTKSPLFMGKVVNPTQK-COOH | 26 |

6.2 Epitope Mapping by Dot Blotting

In this example, dot blotting method was used to identify the MAT eiptope(s) recognized by any of the monoclonal antibodies of Example 2. Briefly, the synthetic A1AT peptides of Example 6.1 were respectively spotted onto a nitrocellulose membrane (10 μg/dot), allowed the membrane to dry, then blocked non-specific sites by soaking the membrane in 5% BSA in TBS-T solution (0.05% Tween 20 in TBS, which includes 20 mM Tris HCl, 150 mM NaCl, pH 7.5) at room temperature for 0.5 to 1 hour. Incubated the dots with the monoclonal antibodies of Example 2 (1:1,000 dilution) at room temperature for at least 30 minutes. Washed the membrane 3 times with TBS-T. Applied secondary antibodies (i.e., goat anti-mouse IgG) conjugated with horseradish peroxidase (HRP) (1:3,000 dilution) to each dot and incubated at room temperature for another 30 minutes. Washed the membrane 3 times with TBS-T, and once with TBS. Applied ECL reagent to each dots for 1 min and exposed X-ray film in the dark room. Compared signals from each dots to that of a standard. Two standards were used in this study, they were A1AT (0.5 μg) and N protein standard (1 μg), respectively. Results were illustrated in FIGS. 5 and 6.

Figure 5:
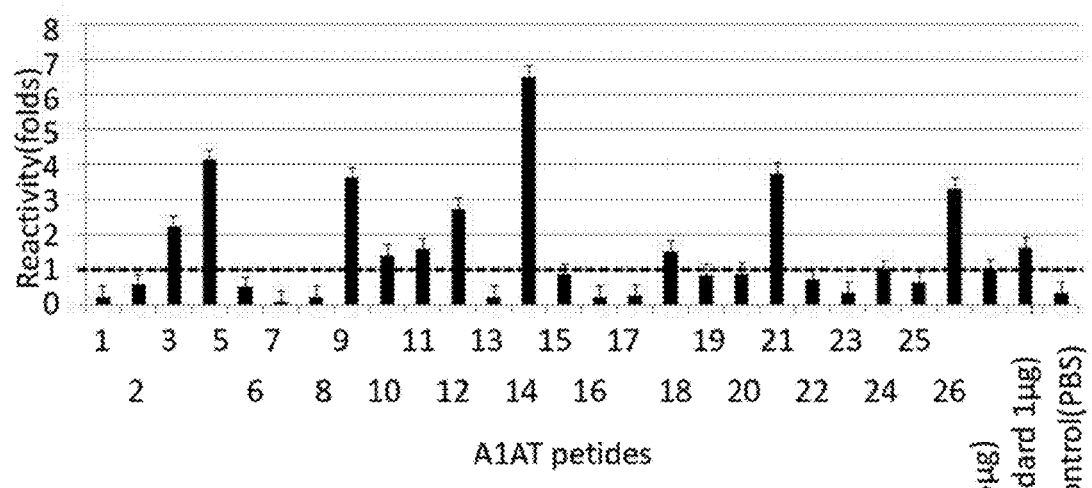
FIG. 5 illustrates the reactivity of the monoclonal antibody 2A7 towards the synthetic A1AT peptides of Example 6.1 in accordance with one embodiment of this invention, in which A1AT (0.5 μg) and N protein standard (1 μg) were included as the standard.
Figure 6:
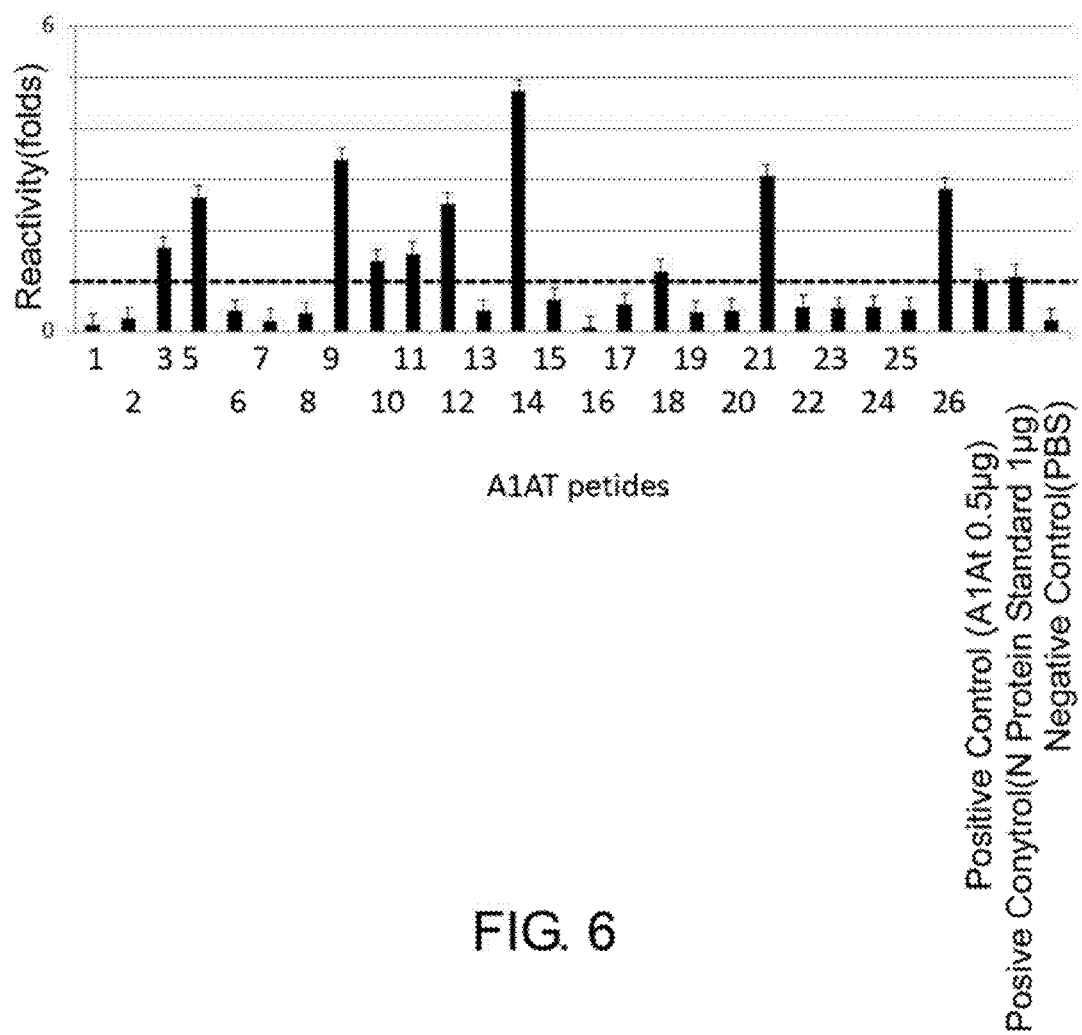
FIG. 6 illustrates the reactivity of the monoclonal antibody 2C8 towards the synthetic A1AT peptides of Example 6.1 in accordance with one embodiment of this invention, in which A1AT (0.5 μg) and N protein standard (1 μg) were included as the standard.

As depicted in FIG. 5, the monoclonal antibody 2A7 exhibited 1-2 folds reactivity towards peptides 10, 11, 18 or 24, and over 2 folds reactivity with peptides 3, 5, 9, 12, 14, 21, and 26, respectively. Similarly, the monoclonal antibody 2C8 exhibited 1-2 folds reactivity with peptides 3, 10, 11 or 18; and more than 2 folds reactivity with peptides 5, 9, 12, 14, 21 or 26 (FIG. 6).

6.3 Epitope Mapping by Competitive ELISA

Peptides 3, 14 and 21 from Example 6.2 were selected and competitive enzyme-linked immunosorbent assay (ELISA) was conducted for the determination of the A1AT epitope recognized by the monoclonal antibody of Example 2. Briefly, in a 96-well plate, mixed various concentrations of monoclonal antibody of Example 2 (2A7 or 2C8) with peptides 3, 14 or 21, and allowed them to form complex at 4° C., then washed the complex with PBS solution 3 times. Applied secondary antibody (i.e., rabbit anti-mouse IgG) conjugated with HRP and further incubated the mixture at room temperature for 1 hour. Washed the plate 3 times with PBS, then a TMB (3,3',5,5'-tetramethylbenzidine) substrate solution was added to each well, allowed the mixture to incubate at 37° C. for 15 minutes, while protecting them from light. A stop solution (i.e., 0.1N HCl) was added to each well and run a microplate reader to take measurements at 450 nm. The molar ratio of A1AT:monoclonal antibody of Example 2:peptide was about 1:0.5:1, 1:0.5:2, 1:0.5:3, 1:0.5:5, 1:0.5:10, 1:0.5:20, 1:0.5:50 and 1:0.5:100, respectively. Results were illustrated in FIGS. 7 and 8.

Figure 7:
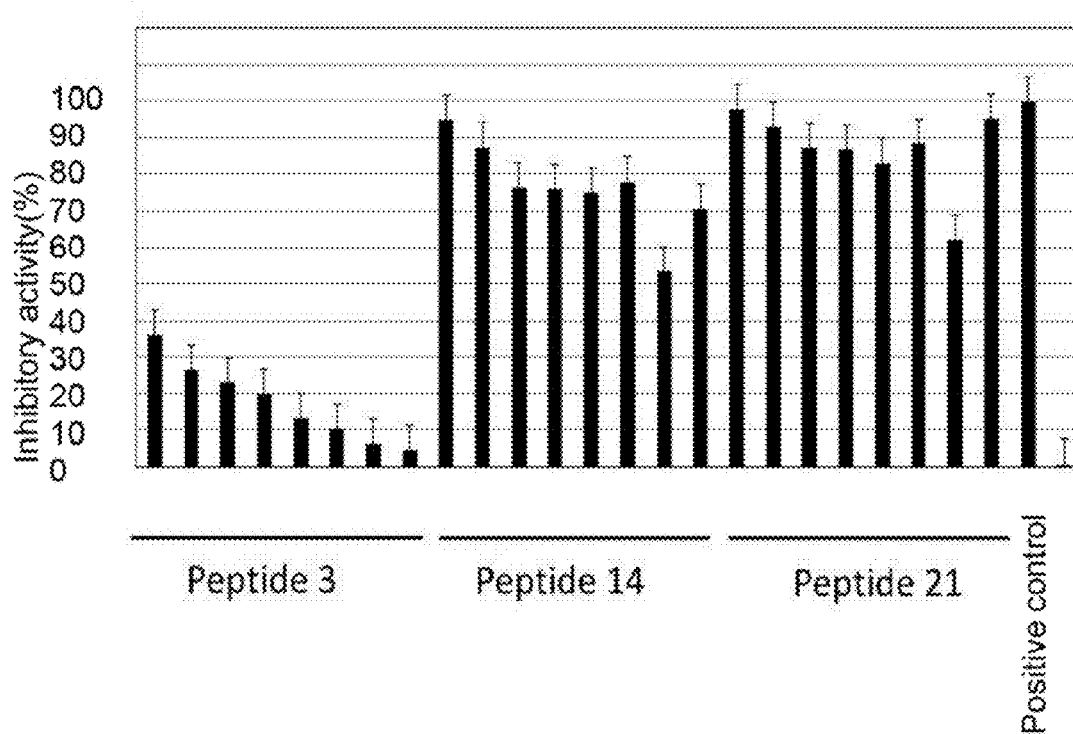
FIG. 7 illustrates the competitive binding of monoclonal antibody 2A7 between A1AT and the synthetic peptide 3, 14 or 21 in accordance with one embodiment of this invention, in which the molar ratio of A1AT:monoclonal antibody 2A7:the synthetic peptide was 1:0.5:1, 1:0.5:2, 1:0.5:3, 1:0.5:5, 1:0.5:10, 1:0.5:20, 1:0.5:50 and 1:0.5:100, respectively.
Figure 8:
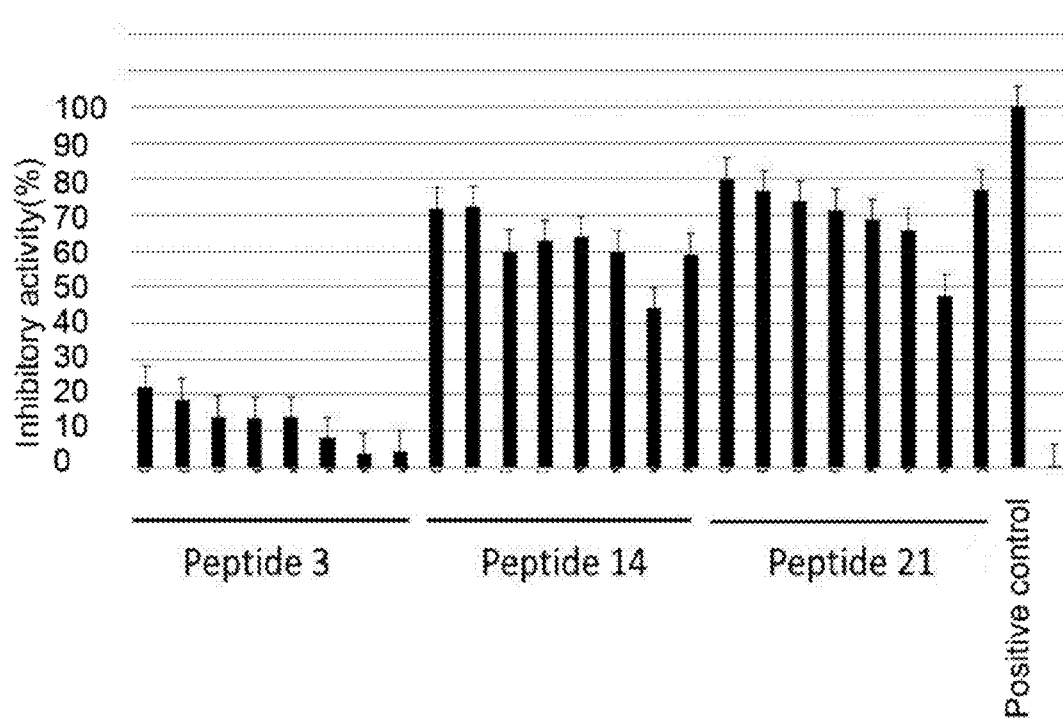
FIG. 8 illustrates the competitive binding of monoclonal antibody 2C8 between A1AT and the synthetic peptide 3, 14 or 21 in accordance with one embodiment of this invention, in which the molar ratio of A1AT:monoclonal antibody 2A7:the synthetic peptide was 1:0.5:1, 1:0.5:2, 1:0.5:3, 1:0.5:5, 1:0.5:10, 1:0.5:20, 1:0.5:50 and 1:0.5:100, respectively.

As depicted in FIGS. 7 and 8, peptide 3 is capable of competing with A1AT for the monoclonal antibody of example 2, with its binding capability decreased along with an increase in the peptide concentration. The results indicated that both 2A7 and 2C8 may recognize the same A1AT epitope represented by peptide 3.

6.4 The Derived Peptide of Peptide 3

Figure 9:
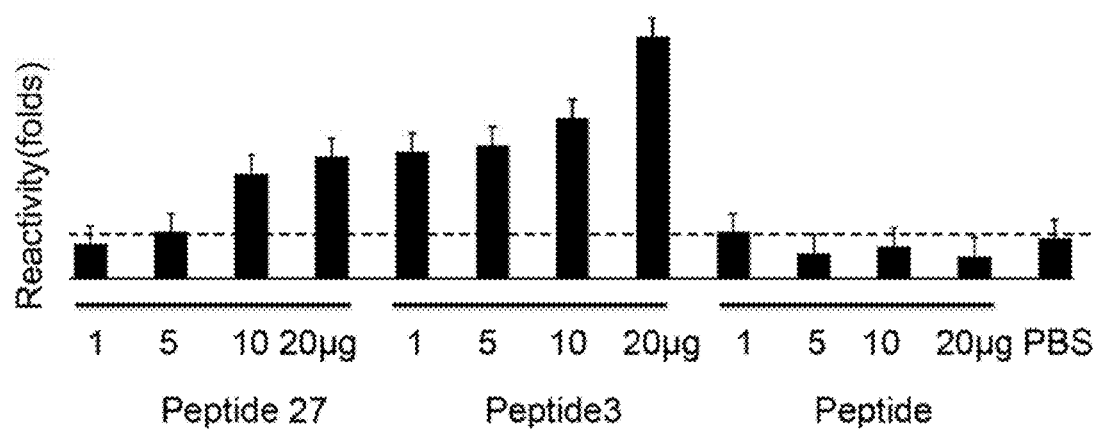
FIG. 9 illustrates the reactivity of the monoclonal antibody 2A7 towards the synthetic A1AT peptides, including P-3, P-21 and P-27 at doses of 1, 5, 10 or 20 μg in accordance with one embodiment of this invention, in which PBS was used as a control.
Figure 10:
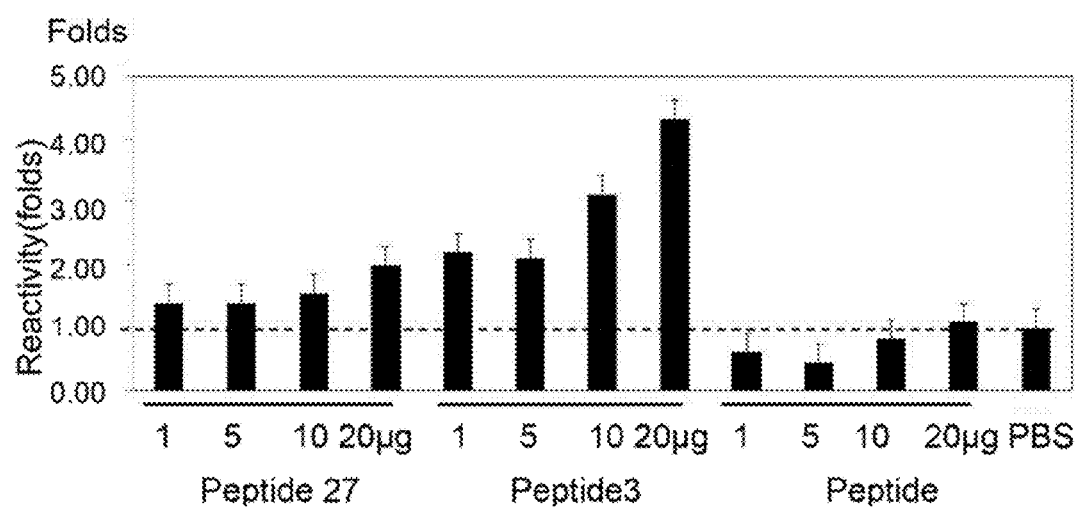
FIG. 10 illustrates the reactivity of the monoclonal antibody 2C8 towards the synthetic A1AT peptides, including P-3, P-21 and P-27 at doses of 1, 5, 10 or 20 μg in accordance with one embodiment of this invention, in which PBS was used as a control.

In view of the results of example 6.3, a smaller peptide (i.e., Peptide 27 or P-27) having only 10 amino acid residues, i.e., H₂N-SLYRQLAHQS-COOH (SEQ ID No: 27, which corresponds to amino acid residues 60-69 of A1AT), was designed based on the sequence of Peptide 3, and further subject to dot blot assay as described above. Results are presented in FIGS. 9 and 10. As depicted in FIG. 9, this peptide (P-27) was able to react with monoclonal antibody 2A7 of this invention, with its reactivity increases about 2 folds, as compared with that of the control. Similar results were also found for monoclonal antibody 2C8 of this invention, reactivity increases for about 1 fold, as compared with that of the control (FIG. 10).

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A monoclonal antibody which specifically binds to an epitope of an isoform of alpha 1-antitrypsin (A1AT) having a molecular weight of about 72 kDa or 58 kDa in a biological sample of a subject, wherein the epitope consists of an amino acid sequence of SEQ ID NO: 3.

2. The monoclonal antibody of claim 1, wherein the antibody is an IgG1.

3. The monoclonal antibody of claim 1, wherein the biological sample is a biopsy sample, a whole blood sample, a plasma sample, a serum sample, a peritoneal fluid, or purified or filtered forms thereof.

4. The monoclonal antibody of claim 3, wherein the biological sample is the serum sample.

5. A method of diagnosing endometriosis in a subject comprising,
obtaining a biological sample of the subject;
contacting the biological sample with the monoclonal antibody of claim 1;
detecting the binding of the monoclonal antibody of claim 1 with the isoform of A1AT having a molecular weight of about 72 kDa or 58 kDa in the biological sample; and
comparing the binding of the monoclonal antibody of claim 1 with the isoform of A1AT having a molecular weight of about 72 kDa or 58 kDa in the biological sample with that of a control, which is a biological sample of a healthy subject;
wherein an increase in the binding of the monoclonal antibody of claim 1 with the isoform of A1AT having a molecular weight of about 72 kDa or 58 kDa in the biological sample as compare with that of the control indicates that the subject has endometriosis.

6. The method of claim 5, wherein the biological sample is a biopsy sample, a whole blood sample, a plasma sample, a serum sample, a mucus sample, or purified or filtered forms thereof.

7. The method of claim 6, wherein the biological sample is the serum sample.

8. A diagnostic kit for detecting an isoform of A1AT having a molecular weight of about 72 kDa or 58 kDa in a biological sample of a subject comprising,
the monoclonal antibody of claim 1;
an agent suitable for detecting the binding of the monoclonal antibody of claim 1 with an epitope of an isoform of alpha 1-antitrypsin (A1AT) in the biological sample of the subject, wherein the epitope consists of an amino acid sequence of SEQ ID NO: 3; and
a legend associated with the kit and indicating how to use the kit.

9. The diagnostic kit of claim 8, wherein the biological sample is a biopsy sample, a whole blood sample, a plasma sample, a serum sample, a peritoneal fluid, or purified or filtered forms thereof.

10. The diagnostic kit of claim 9, wherein the biological sample is the serum sample.

* * * * *